United States Patent [19]

Spivack et al.

[11] Patent Number: 4,503,243
[45] Date of Patent: Mar. 5, 1985

[54] DIOXASILEPIN AND DIOXASILOCIN STABILIZERS

[75] Inventors: John D. Spivack; Stephen D. Pastor, both of Spring Valley, N.Y.

[73] Assignee: Eisai Co., Ltd., Tokyo, Japan

[21] Appl. No.: 457,349

[22] Filed: Jan. 12, 1983

[51] Int. Cl.³ .............................. C07F 7/08; C07F 7/18
[52] U.S. Cl. ...................... 556/427; 556/464; 556/428; 524/261; 524/262; 524/265
[58] Field of Search .................. 556/428, 464, 427

[56] References Cited

U.S. PATENT DOCUMENTS

| | | | |
|---|---|---|---|
| 2,964,499 | 12/1960 | Weigel et al. | 556/464 X |
| 2,983,745 | 5/1961 | Speier | 556/464 X |
| 3,083,219 | 3/1963 | Anderson | 556/464 |
| 3,256,308 | 6/1966 | Sterling et al. | 556/464 |
| 4,252,967 | 2/1981 | Jung et al. | 556/464 X |
| 4,447,628 | 5/1984 | Farnham | 556/464 X |

FOREIGN PATENT DOCUMENTS

| | | | |
|---|---|---|---|
| 214535 | 3/1968 | U.S.S.R. | 556/464 |
| 467078 | 4/1975 | U.S.S.R. | 556/464 |

OTHER PUBLICATIONS

Perozzi et al., "J.A.C.S.", 107, No. 6, pp. 1591–1593, 1949.

*Primary Examiner*—Paul F. Shaver
*Attorney, Agent, or Firm*—Wenderoth, Lind & Ponack

[57] ABSTRACT

Hindered silane compounds of the formula

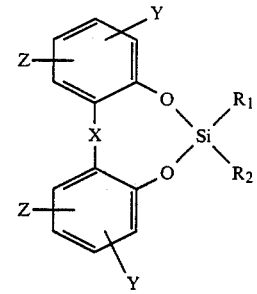

are prepared by the reaction of the appropriate silane and phenol compounds, said hindered silanes being useful as stabilizers of organic polymers such as polyolefins, vinyl halide polymers, elastomers, polyesters and polycarbonates.

16 Claims, No Drawings

DIOXASILEPIN AND DIOXASILOCIN STABILIZERS

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Silanes are disclosed in a number of publications. Unsubstituted dibenzo[d,f][1,3,2]dioxasilocin ring systems, i.e. biphenyl compounds without substituents on the phenyl rings, have been disclosed in British Pat. No. 857,153, German Pat. No. 1,057,129, Chemical Abstracts 62, 1683 (1965), Chemical Abstracts 50, 3336 (1955), and Roshdy et al, Z. Naturforsch 18b, 1124 (1963). These compounds are disclosed for use as organic intermediates and as comonomers for heat-resistant plastics. Roshdy indicates that these compounds are heat stable. The stabilizing effectiveness of the compounds is not mentioned. Tetrakis(4-hydroxy-3,5-di-tert.butylphenyl-alkoxy)silanes and similar derivatives based on the reaction between 2,6-di-tert-butylphenol and silicon tetrachloride are disclosed in Ershov et al., Izv. Akad. Nauk SSSR, Ser. Khim 6, 14 (1972) and Gorodetskaya et al., International Polymer Science and Technology 6, No. 1, T54–T55 (1979). The compounds are disclosed as heat stabilizers for polypropylene.

It has now been determined that the hindered silane derivatives of this invention possess an unusual combination of desirable properties which makes them particularly effective and useful as stabilizers. The compounds are particularly effective in protecting polyolefins and polyvinyl chloride.

It is the primary object of this invention to provide a class of hindered silanes which exhibit a broad range of improved stabilization performance characteristics.

Various other objects and advantages of this invention will become evident from the following description thereof.

The hindered silane compounds of this invention correspond to the formula.

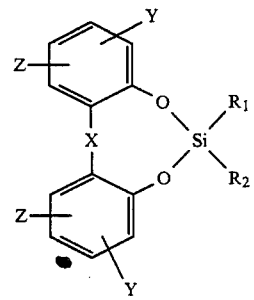

wherein $R_1$ and $R_2$ independently are hydrogen, alkyl of 1 to 4 carbon atoms or phenyl; or $R_1$ and $R_2$ together form

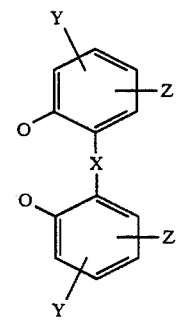

X is a direct bond, alkylidene of 1 to 7 carbon atoms or sulfur;

Y is alkyl of 4 to 12 carbon atoms or alkaryl of 7 to 12 carbon atoms; and

Z is hydrogen, alkyl from 1 to 12 carbon atoms or phenyl.

Preferred compounds within the above structure are those wherein Y is in the ortho position to the silane oxygen in each of the phenyl rings.

The Y and Z groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the Z group to be in the para position to oxygen, particularly if Z is tert-alkyl.

X is preferably lower alkylidene of the formula

wherein $R_3$ and $R_4$ are independently hydrogen or alkyl of 1 to 4 carbon atoms, provided that the number of carbon atoms does not exceed 7; or sulfur.

Alkaryl substituents are generally derived from tolyl, mesityl and xylyl.

The silanes of this invention can be prepared by reacting the appropriately substituted halosilane with an alkylated 2,2'-biphenol or an alkylated 2,2'-alkylidene-bis-phenol optionally in a solvent to yield the desired product. The solvent is preferably aromatic, such as benzene, toluene, xylene and the like, or heterocyclic ether such as tetrahydrofuran. The reaction temperature ranges from 0° C. to room temperature. The preferred method for preparing the compounds of this invention involves reacting the halosilane, primarily the dichloro-silane, with the appropriate phenol in the presence of a proton acceptor such as a tertiary amine, for example, triethylamine or pyridine.

The starting materials needed to prepare these hindered silane compounds are items of commerce or can be prepared by known methods.

The silane starting materials correspond to the formula

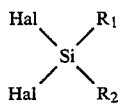

wherein Hal is halogen, preferably chlorine, and $R_1$ and $R_2$ are as previously defined, preferably hydrogen, methyl or phenyl, and additionally halogen. As to the latter, the tetrachlorosilane is utilized to prepare the symmetrical bis(dibenzo-dioxa) compound.

The phenol starting materials correspond to the formula

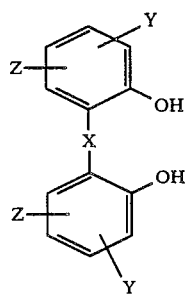

wherein X, Y and Z are as previously defined. Typical X members include a direct bond, methylene, ethylidene and sulfur; typical Y and Z members include tert. butyl.

Compounds of this invention are effective in stabilizing organic materials such as plastics, polymers and resins. The compounds of the invention are particularly useful as stabilizers, especially for the protection of polyolefins, for instance, polyethylene, polypropylene, polyisobutylene, poly(butene-1), poly(pentene-1), poly(3-methylbutene-1), poly(4-methyl-pentene-1), various ethylene-propylene copolymers and the like; and poly(vinyl chloride).

Other substrates in which the compounds of this invention are particularly useful are polystyrene, including impact polystyrene, ABS resin, SBR, polyisoprene, as well as natural rubber, polyesters, including polyethylene terephthalate and polybutylene terephthalate, and including copolymers.

Polyurethanes, polycarbonates, polyamides such as nylon 6, 6/6 and the like as well as copolyamides and polysulfones are also stabilized.

In general, polymers which can be stabilized include:

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyethylene or with polyisobutylene.

3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.

4. Polystyrene.

5. Random copolymers of styrene of α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene or polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamides and polyacrylonitrile.

9. Copolymers from the monomers mentioned under 8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.

10. Polymers which are derived from unsaturated alcohols and amines, or acyl derivatives therof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acids and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyether-esters derived from polyethers having hydroxyl end groups.

18. Polycarbonates.

19. Polysulfones and polyethersulfones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides and aromatic diepoxides.

26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methylcellulose.

27. Naturally occurring and synthetic organic materials which are pure monomeric compounds or mixtures of such compounds, for example mineral oils, animal and vegetable fats, oils and waxes, or oils, fats and waxes based on synthtic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

28. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2.6-dialkylphenols, such as, for example, 2,6-ditert.-butyl-4-methylphenol, 2-tert.-butyl-4,6-dimethylphenol, 2,6-di-tert.-butyl-4-methoxymethylphenol and 2,6-di-octadecyl-4-methylphenol.

1.2. Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,6-di-tert.-butyl-4-hydroxy-anisole, 3,5-di-tert.-butyl-4-hydroxy-anisole, tris-(3,5-di-tert.-butyl-4-hydroxyphenyl)phosphite, 3,5-di-tert.-butyl-4-hydroxyphenyl stearate and bis-(3,5-di-tert.-butyl-4-hydroxyphenyl)adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxy-phenyl)disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5. O-, N- and S-benzyl compounds, such as, for example, 3,3',5,5'-tetra-tert.-butyl-4,4'-dihydroxydibenzyl ether, octadecyl 4-hydroxy-3,5-dimethylbenzylmercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6. Hydroxybenzylated malonates, such as, for example, dioctadecyl 2,2-bis-(3,5-di-tert.-butyl-2-hydroxybenzyl)malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7. Hydroxybenzyl-aromatic comounds, such as, for example, 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.- butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

1.9. Amides of β-(3,5-di-tert.-butyl-4-hydroxyphenyl) propionic acid, such as, for example, 1,3,5-tris-3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-bis-β-(3,5-di-t-butyl-4-hydroxyphenylpropionyl)-hydrazine.

1.10. Esters of β-(3,5-di-tert.-butyl-4-hydroxyphenyl) propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11. Esters of β(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol trimethyolethane, trimethylolpropane, tris-hydroxyethyl isocyanurate and 4p-hydroxymethyl-1-phospha-2,6,7-trioxabicyclo[2,2,2]octane.

1.12. Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane, especially the tetra-bis ester of pentaerythritol.

1.13. Benzylphosphonates, such as, for example, dimethyl 3,5-di-tert.-butyl-4-hydroxybenzyl-phosphonate, diethyl 3,5-di-tert.butyl-4-hydroxybenzyl-phosphonate, dioctadecyl 3,5-di-tert.butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-napthylamine, phenyl-2-naphthylamine, N,N'-di-phenyl-p-phenylenediamine, N,N'-di-2-naphthyl-p-phenylenediamine, N,N'-di-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline.

Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2'-Hydroxyphenyl)-benzotriazoles, e.g. the 5'-methyl-, 3',5'-di-tert.-butyl-, 5'-tert.butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-alpha-methylbenzyl-5'-methyl-, 3'-alpha-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl-, 3',5'-bis(alpha,alpha-dimethylbenzyl), 3',5'-bis(alpha,alpha-dimethyl benzyl)-5-chloro-, 3',5'-di-tert.-octylphenyl, 3',5'-di-tert.-octylphenyl-5-chloro- and 5-chloro-3',5'-di-tert.-amyl-derivatives.

2.2. 2,4-bis-(2'-Hydroxyphenyl)-6-alkyl-s-triazines, e.g. the 6-ethyl-, 6-heptadecyl- or 6-undecyl-derivative.

2.3 2-Hydroxybenzophenones, e.g. the 4-hydroxy-, 4-methoxy-, 4-octoxy-, 4-decyloxy-, 4-dodecyloxy-, 4-benzyloxy-, 2',4-4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester or N-(β-carbomethoxyvinyl)-2-methyl-indoline.

2.7. Sterically hindered amines, e.g. 4-benzoyl-2,2,6,6-tetramethylpiperidine, 4-stearyl-oxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decane-2,4-dione.

2.8. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-plamitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl)phosphite, trilauryl phosphite, trioctadecyl phosphite, 3,9-isodecyloxy-2,4,8,10-tetraoxa-3,9-diphospha spiro[5,5]undecane and tri-(4-hydroxy-3,5-di-tert.butylphenyl)phosphite.

Other additives that can be incorporated in the stabilized compositions are thiosynergists such as dilaurylthiodipropionate or distearylthiodipropionate, lubricants such as stearyl alcohol fillers, carbon black, asbestos, kaolin, talc, glass fibers, pigments, optical brighteners, flameproofing agents and antistatic agents.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

The following examples further illustrate the embodiments of this invention. In these examples, all parts given are by weight unless otherwise specified.

EXAMPLE 1

2,4,8,10-Tetra-t-butyl-6-methyl-dibenzo[d,f][1,3,2]dioxasilepin

In a flame-dried flask under a dry nitrogen atmosphere, a stirred solution of 23.0 grams (0.20 mole) of dichloromethylsilane in 200 ml toluene is treated slowly with a solution of 82.1 grams (0.20 mole) of 3,3',5,5'-tetra-tert-butyl-biphenyl-2,2'-diol and 40.5 grams (0.40 mole) of triethylamine in 250 ml toluene at 5°–10° C. The reaction mixture is stirred at room temperature for 12 hours following the addition, is then filtered to remove triethylamine hydrochloride, and the solvent removed in vacuo. The residue is recrystallized from acetonitrile-toluene giving 69.4 grams (77%) of white crystals, mp 191°–198° C.

Anal. Calcd. for $C_{29}H_{44}O_2Si$: C, 76.9; H, 9.8. Found: C, 77.0; H, 9.8.

EXAMPLE 2

2,4,8,10-Tetra-t-butyl-6,6-dimethyl-dibenzo[d,f][1,3,2]dioxasilepin

Utilizing procedure of Example 1, this compound is prepared from 25.8 grams (0.20 mole) dichlorodimethylsilane, 82.1 grams (0.20 mole) 3,3',5,5'-tetra-tert-butyl-biphenyl-2,2'-diol and 40.5 grams (0.40 mole) of triethylamine. Recrystallization from 2-butanone gives 43.7 grams (47%) of a white powder, mp 170°–176° C.

Anal. Calcd. for $C_{30}H_{46}O_2Si$: C, 77.2; H, 9.9. Found: C, 77.4; H, 10.0.

EXAMPLE 3

2,4,8,10-Tetra-t-butyl-6-methyl-12H-dibenzo[d,g][1,3,2]dioxasilocin

Utilizing the procedure of Example 1, this compound is prepared from 23.0 grams (0.20 mole) dichloromethylsilane, 84.9 grams (0.20 mole) of 2,2-methylenebis(6-di-t-butylphenol) and 40.5 grams (0.40 mole) of triethylamine. Recrystallization twice from acetonitrile-toluene gives 15.5 grams (17%) of white powder, mp 230°–231° C.

Anal. Calcd. for $C_{30}H_{46}O_2Si$: C, 77.2; H, 9.9 Found C, 77.2; H, 9.7.

EXAMPLE 4

2,4,8,10-Tetra-t-butyl-6-phenyl-12H-dibenzo[d,g][1,3,2]dioxasilocin

Utilizing the procedure of Example 1, this compound is prepared from 17.7 grams (0.1 mole) of dichlorophenylsilane, 42.5 grams (0.1 mole) of 2,2'-methylenebis(4,6-di-t-butylphenol) and 20.2 grams (0.20 mole) of triethylamine. Recrystallization twice from acetonitrile-toluene yields 34.0 grams (64% yield) of product as an off white powder, mp 153°–156° C.; IR: 2200 $cm^{-1}$ SiH.

Analysis calculated for $C_{35}H_{48}O_2Si$: C, 79.5; H, 9.2. Found: C, 79.9; H, 9.0.

EXAMPLE 5

2,4,8,10-Tetra-t-butyl-6,6,12-trimethyl-12H-dibenzo[d,g][1,3,2]dioxasilocin

Utilizing the procedure of Example 1, this compound is prepared from 25.8 grams (0.20 mole) of dichlorodimethylsilane, 87.7 grams (0.20 mole) of 2,2'-ethylidene-bis(4,6-di-t-butylphenol) and 40.5 grams (0.40 mole) of triethylamine. Recrystallization from acetonitrile-toluene yields 77.7 g (79% yield) of product as white needles, mp 171°–177° C.

Analysis calculated for $C_{32}H_{50}O_2Si$: C, 77.7; H, 10.2. Found: C, 77.5; H, 9.9.

EXAMPLE 6

2,4,8,10-Tetra-t-butyl-6,12-dimethyl-12H-dibenzo[d,g][1,3,2]dioxasilocin

Utilizing the procedure of Example 1, this compound is prepared from 23.0 grams (0.20 mole) dichloromethylsilane, 87.7 grams (0.20 mole) 2,2'-ethylidene-bis(4,6-di-t-butylphenol) and 40.5 grams (0.40 mole) of triethylamine. Recrystallization twice from acetonitrile-toluene gives 49.0 g (51% yield) of white crystals, mp 189°–194° C.

Anal. Calcd. for $C_{31}H_{48}O_2Si$: C, 77.4; H, 10.1. Found: C, 77.1; H, 9.9.

EXAMPLE 7

2,4,8,10-Tetra-t-butyl-6-methyl-dibenzo[d,g][1,3,2,6]dioxasilathiocin

Utilizing the procedure of Example 1, this compound is prepared from 5.7 grams (0.05 mole) dichloromethylsilane, 22.1 grams (0.05 mole) 2,2'-thiobis(4,6-di-t-butylphenol), and 10.1 grams (0.10 mole) triethylamine. Recrystallization twice from acetone-toluene gives 11.8 grams (48% yield) of white crystals, mp 178°–180° C.

Anal. Calcd. for $C_{29}H_{44}O_2SSi$: C, 71.9; H, 9.2. Found: C, 71.7; H, 9.2.

EXAMPLE 8

2,4,8,10-Tetra-t-butyl-6-phenyl-dibenzo[d,g][1,3,2,6]dioxasilathiocin

Utilizing the procedure of Example 1, this compound is prepared from 5.3 grams (0.03 mole) dichlorophenylsilane, 13.3 grams (0.03 mole) 2,2'-thio-bis(4,6-di-t-butylphenol), and 6.1 grams (0.06 mole) triethylamine. Recrystallization from acetone gives 6.7 grams (41% yield) of white solid, mp 175°–177° C.

Anal. Calcd. for $C_{34}H_{46}O_2SSi$: C, 74.7; H, 8.5. Found: C, 74.9; H, 8.6.

EXAMPLE 9

2,4,8,10-Tetra-t-butyl-12H-dibenzo[d,g][1,3,2]dioxasilocin

In a flame-dried flask equiped with a dry ice-acetone filled Dewar condenser and a sintered glass inlet, 42.5 grams (0.1 mole) 2,2'-methylene-bis(4,6-di-t-butylphenol) and 20.2 grams (0.2 mole) triethylamine dissolved in 100 ml tetrahydrofuran are treated slowly with 11.1 grams (0.11 mole) dichlorosilane. Filtration and recrystallization from acetonitrile-toluene gave 25.9 grams (57% yield) of a white solid mp 189°–192° C. The $^1$H NMR spectrum is consistent with the product.

EXAMPLE 10

Unstabilized polypropylene powder (Hercules Profax 6501) is thoroughly blended with 0.3%, by weight, of additive. The blended materials are then milled on a two-roll mill at 182° C. for 5 minutes, after which time the stabilized polypropylene is sheeted from the mill and allowed to cool. The milled polypropylene is then cut into pieces and compression molded on a hydraulic press at 220° C. at 175 p.s.i. (1.2×0.06 Pa) into 25 mil (0.635 mm) thick plaques. The samples are exposed in a fluorescent sunlight/black light chamber and observed for failure. Failure is taken as the hours required to reach 0.5 carbonyl absorbance by infrared spectroscopy on the exposed films.

| Additive | FS/BL Test (hours to failure) |
| --- | --- |
| None | 50–100 |
| Example 1 | 280 |
| Example 2 | 270 |
| Example 3 | 340 |
| Example 4 | 400 |
| Example 5 | 360 |
| Example 6 | 350 |
| Example 7 | 470 |
| Example 8 | 450 |
| Example 9 | 770 |

EXAMPLE 11

The following polyvinyl chloride formulation is prepared.

|  | Parts |
| --- | --- |
| polyvinyl chloride | 100.0 |
| epoxidized soy bean oil | 4.0 |
| calcium stearate | 0.35 |
| zinc stearate | 0.15 |
| lubricant | 0.7 |
| flow modifier | 0.5 |
| impact modifier | 8.0 |
| phenyl di-dodecyl phosphite | 0.3 |
| compound of Example 1 | 0.6 |

Compression molded test plaques are prepared and oven aged at 125° C. The stabilized plaques exhibit improved color over the control polyvinyl chloride formulation, i.e. the formulation absent the stabilizer.

Summarizing, it is seen that this invention provides novel hindered silane compounds which exhibit effective stabilization activity. Variation may be made in proportions, procedures and materials without departing from the scope of the invention as defined by the following claims.

What is claimed is:

1. A compound of the formula

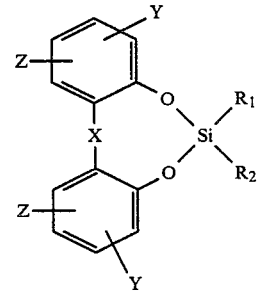

wherein

R$_1$ and R$_2$ independently are hydrogen, alkyl of 1 to 4 carbon atoms or phenyl; or R$_1$ and R$_2$ together form

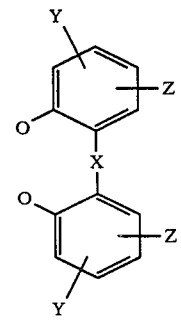

X is a direct bond, alkylidene of 1 to 7 carbon atoms or sulfur;

Y is alkyl of 4 to 12 carbon atoms or alkaryl of 7 to 12 carbon atoms; and

Z is hydrogen, alkyl from 1 to 12 carbon atoms or phenyl.

2. The compound of claim 1, wherein Y is in the ortho position to the silane oxygen in each of the phenyl rings.

3. The compound of claim 2, wherein Y is alkyl of 4 to 8 carbon atoms.

4. The compound of claim 3, wherein Y is tert-butyl.

5. The compound of claim 2, wherein Z is tert-alkyl of 4 to 8 carbon atoms and is in the para position to the silane oxygen in each of the phenyl rings.

6. The compound of claim 2, wherein X is alkylidene of 1 to 7 carbon atoms or sulfur.

7. The compound of claim 6, wherein X is alkylidene of the formula

wherein R$_3$ and R$_4$ independently are hydrogen or alkyl of 1 to 4 carbon atoms, provided that the number of carbon atoms does not exceed 7.

8. 2,4,8,10-Tetra-t-butyl-6-methyl-dibenzo[d,f][1,3,2-]dioxasilepin, according to claim 2.

9. 2,4,8,10-Tetra-t-butyl-6,6-dimethyl-dibenzo[d,f][1,3,2]dioxasilepin, according to claim 2.

10. 2,4,8,10-Tetra-t-butyl-6-methyl-12H-dibenzo[d,g][1,3,2]dioxasilocin, according to claim 2.

11. 2,4,8,10-Tetra-t-butyl-6-phenyl-12H-dibenzo[d,g][1,3,2]dioxasilocin, according to claim 2.

12. 2,4,8,10-Tetra-t-butyl-6,6,12-trimethyl-12H-dibenzo[d,g][1,3,2]dioxasilocin, according to claim 2.

13. 2,4,8,10-Tetra-t-butyl-6,12-dimethyl-12H-dibenzo[d,g][1,3,2]dioxasilocin, according to claim 2.

14. 2,4,8,10-Tetra-t-butyl-6-methyl-dibenzo[d,g][1,3,2,6]dioxasilathiocin, according to claim 2.

15. 2,4,8,10-Tetra-t-butyl-6-phenyl-dibenzo[d,g][1,3,2,6]dioxasilathiocin, according to claim 2.

16. 2,4,8,10-Tetra-t-butyl-12H-dibenzo[d,g][1,3,2]dioxasilocin, according to claim 2.

* * * * *

UNITED STATES PATENT AND TRADEMARK OFFICE
CERTIFICATE OF CORRECTION

PATENT NO. : 4,503,243

DATED : March 5, 1985

INVENTOR(S) : John D. Spivack and Stephen D. Pastor

It is certified that error appears in the above-identified patent and that said Letters Patent is hereby corrected as shown below:

The cover page of the patent, Item [73] Assignee:

should read:

-- CIBA-GEIGY Corporation --.

Signed and Sealed this

Fifth Day of November 1985

[SEAL]

Attest:

Attesting Officer

DONALD J. QUIGG

Commissioner of Patents and Trademarks